(12) United States Patent
Lee et al.

(10) Patent No.: US 10,617,814 B2
(45) Date of Patent: Apr. 14, 2020

(54) INFUSION POUCH SET WITH BUILT-IN INJECTION MEDICINE BOTTLE HAVING VIAL FUNCTION

(71) Applicant: JCTECH CO., LTD., Incheon (KR)

(72) Inventors: Young-jae Lee, Seoul (KR); Ho-jae Lee, Bucheon-si (KR)

(73) Assignee: JCTECH CO., LTD. (KR)

( * ) Notice: Subject to any disclaimer, the term of this patent is extended or adjusted under 35 U.S.C. 154(b) by 175 days.

(21) Appl. No.: 15/841,730

(22) Filed: Dec. 14, 2017

(65) Prior Publication Data

US 2019/0184096 A1 Jun. 20, 2019

(51) Int. Cl.
| | |
|---|---|
| *A61M 5/14* | (2006.01) |
| *A61M 5/158* | (2006.01) |
| *A61M 5/168* | (2006.01) |
| *A61J 1/14* | (2006.01) |
| *A61J 1/20* | (2006.01) |
| *A61M 5/162* | (2006.01) |

(52) U.S. Cl.
CPC .......... *A61M 5/1407* (2013.01); *A61J 1/1412* (2013.01); *A61J 1/20* (2013.01); *A61M 5/1414* (2013.01); *A61M 5/158* (2013.01); *A61M 5/168* (2013.01); *A61M 5/162* (2013.01)

(58) Field of Classification Search
CPC .. A61M 5/1407; A61M 5/1414; A61M 5/162; A61J 1/20; A61J 1/1412
See application file for complete search history.

(56) References Cited

U.S. PATENT DOCUMENTS 7,425,209 B2 * 9/2008 Fowles ................. A61J 1/1406
604/403

* cited by examiner

*Primary Examiner* — Bradley J Osinski
(74) *Attorney, Agent, or Firm* — Park & Associates IP Law, P.C.

(57) ABSTRACT

An infusion pouch set with a built-in injection medicine bottle having a vial function including: a discharge port 20 provided at an outlet 12 of a pouch container 10; and an injection port 30 provided at an inlet 14 of the pouch container 10; wherein the injection port 30 comprises, an injection needle part 40 configured to have an injection needle 44 provided vertically on an upper part of an injection needle holder 42 which is welded to the inlet 14 of the pouch container 10; an inner cap 50 having a sealing membrane 52 which is coupled to the injection needle holder 42 of the injection needle part 40, accommodates the injection needle 44 therein, and is punctured by the injection needle 44 when lowered; an outer cap 60 which is vertically moveable along the same axis as the inner cap 50 and accommodates an injection medicine bottle 70 in an upside down state therein; and a packing holder 90 which is vertically movably coupled at an upper part of the sealing membrane 52 of the inner cap 50, and a lower part of the packing holder 90 accommodates a packing 80 which hermetically couples an inlet cover 72 with the sealing membrane 52 and has a vertical through-hole 82 at its center.

8 Claims, 4 Drawing Sheets

INFUSION POUCH SET WITH BUILT-IN INJECTION MEDICINE BOTTLE HAVING VIAL FUNCTION

FIELD OF THE INVENTION

The present disclosure relates to an infusion pouch set with a built-in injection medicine bottle that functions as a vial.

BACKGROUND OF THE INVENTION

Korean Granted Patent Publication No. 10-0569223 discloses a configuration which comprises a plastic container provided with, a connecting member that communicates with a drug container and a discharging member that discharges a drug solution at another end; a communicating needle that is connected to the connecting member, and punctures a stopper and the drug container of a protection cap which accommodates the drug container, to be inserted in the connecting member which allows the drug in the drug container to be communicated as an infusion solution; and the protection cap is a combination of a fixed cap and a movable cap, wherein it is difficult to assemble, configured to have complicated components, and has the problem of poor sealability.

As another technical means, Korean Granted Patent Publication No. 10-1640159 discloses that a solution cap is coupled to an inlet of a solution container, a communicating member is provided inside the solution cap, and a drug container is provided above the communicating member and the solution cap to supply the medicine inside the drug container to the solution container by a puncturing needle through the communicating member, via the communicating member and through a needle insertion portion, wherein although it is advantageous in that the two-way injection needle punctures both the solution container and the drug container, there are numerous parts and it is difficult to ensure sealability.

Korean Granted Utility Model Publication No. 20-0455090 discloses a pouch stopper for use in a pouch bag, and Korean Laid-Open Patent Publication No. 10-2006-0123372, Korean Granted Utility Model Publication No. 20-0478043, and Korean Granted Patent Publication No. 10-0569223 discloses a structure of a vial combined with an infusion pouch set. However, these structures have a structure in which the vial is attached to the outside of the infusion container, which results in poor storage, packaging difficulties, and upon impact, the vial medicines can be unintentionally mixed which makes it hard to use, and other problems of the like.

SUMMARY OF THE INVENTION

Therefore, the present disclosure is directed to providing an infusion pouch set with a built-in injection medicine bottle having a vial function, wherein, in a pouch infusion container having an injection port installed at an inlet and an outlet installed at an outlet portion of a pouch container, at a lower part of the injection port, an injection needle protruding vertically is fixed and the injection needle is formed to communicate with the infusion container, an inner cap provided with a sealing membrane at a central portion thereof is coupled to an injection needle holder fixing the injection needle, a vertically movable packing holder is arranged on the sealing membrane of the inner cap and an inlet cover of an injection medicine bottle and a sealing packing are arranged at the packing holder, the packing holder that accommodates the packing and the injection medicine bottle are accommodated in an outer cap which is screw-connected to the inner cap, and when a C-shaped clip that provides a vertical space which allows the outer cap to be lowered from a fixed position is removed and then the outer cap is lowered, when the sealing membrane is lowered as the packing holder and the injection medicine bottle are lowered together with the outer cap, the injection needle punctures the sealing membrane and the injection solution is automatically mixed with the contents of the infusion container, so that it is hygienic, easy to use, and safe.

The present disclosure is also directed to providing an infusion pouch set with a built-in injection medicine bottle having a vial function, wherein, in a pouch infusion container having an injection port installed at an inlet and an outlet installed at an outlet portion of a pouch container, at a lower part of the injection port, an injection needle protruding vertically is fixed and the injection needle is formed to communicate with the infusion container, an inner cap provided with a sealing membrane at a central portion thereof is coupled to an injection needle holder fixing the injection needle, a vertically movable packing holder is arranged on the sealing membrane of the inner cap and an inlet cover of an injection medicine bottle and a sealing packing are arranged at the packing holder, the packing holder that accommodates the packing and the injection medicine bottle are accommodated in an outer cap which is screw-connected to the inner cap, and when a C-shaped clip that provides a vertical space which allows the outer cap to be lowered from a fixed position is removed and then the outer cap is lowered by rotating the outer cap, as like rotating in a screw-connection, to be lowered to the exposed vertical space, when the sealing membrane is lowered as the packing holder and the injection medicine bottle are lowered together with the outer cap, the injection needle punctures the sealing membrane and the injection solution is automatically mixed with the contents of the infusion container, thereby a user doesn't need to manipulate the injection needle separately when puncturing the injection needle to the injection medicine bottle, so it is possible for beginners to use.

In addition, the present disclosure is directed to providing an infusion pouch set with a built-in injection medicine bottle having a vial function, wherein an injection needle is fixed at the inlet of the pouch container, an inner cap having an edge that is welded is coupled to an injection needle holder that supports the injection needle, a sealing membrane which wraps the injection needle is arranged at the inner cap so the injection needle is isolated from outside, completely blocking the infiltration of external bacteria, and a packing holder is provided on the sealing membrane to be used for sealing the injection medicine bottle with an inner packing to completely seal the surroundings of the injection medicine bottle, and before use, the C-shaped clip holds the outer cap at a predetermined height, thereby preventing the sealing membrane from being damaged by the injection needle, thereby being durable.

According to an embodiment of the present disclosure, an infusion pouch set with a built-in injection medicine bottle having a vial function may include, a discharge port provided at an outlet of a pouch container; and an injection port provided at an inlet of the pouch container; and the injection port may include, an injection needle part configured to have an injection needle provided vertically on an upper part of an injection needle holder which is welded to the inlet of the pouch container; an inner cap having a sealing membrane which is coupled to the injection needle holder of the injection needle part, accommodates the injection needle therein, and is punctured by the injection needle when lowered; an outer cap which is vertically moveable along the same axis as the inner cap and accommodates an injection medicine bottle in an upside down state therein; and a packing holder which is vertically movably coupled at an upper part of the sealing membrane of the inner cap and a lower part of the packing holder accommodates a packing which hermetically couples an inlet cover with the sealing membrane and has a vertical through-hole at its center.

As described above, the present disclosure, wherein, in a pouch infusion container having an injection port installed at an inlet and an outlet installed at an outlet portion of a pouch container, at a lower part of the injection port, an injection needle protruding vertically is fixed and the injection needle is formed to communicate with the infusion container, an inner cap provided with a sealing membrane at a central portion thereof is coupled to an injection needle holder fixing the injection needle, a vertically movable packing holder is arranged on the sealing membrane of the inner cap and an inlet cover of an injection medicine bottle and a sealing packing are arranged at the packing holder, the packing holder that accommodates the packing and the injection medicine bottle are accommodated in an outer cap which is screw-connected to the inner cap, and when a C-shaped clip that provides a vertical space which allows the outer cap to be lowered from a fixed position is removed and then the outer cap is lowered, when the sealing membrane is lowered as the packing holder and the injection medicine bottle are lowered together with the outer cap, the injection needle punctures the sealing membrane and the injection solution is automatically mixed with the contents of the infusion container, provides hygiene, convenient use, and safety.

The present disclosure, wherein, in a pouch infusion container having an injection port installed at an inlet and an outlet installed at an outlet portion of a pouch container, at a lower part of the injection port, an injection needle protruding vertically is fixed and the injection needle is formed to communicate with the infusion container, an inner cap provided with a sealing membrane at a central portion thereof is coupled to an injection needle holder fixing the injection needle, a vertically movable packing holder is arranged on the sealing membrane of the inner cap and an inlet cover of an injection medicine bottle and a sealing packing are arranged at the packing holder, the packing holder that accommodates the packing and the injection medicine bottle are accommodated in an outer cap which is screw-connected to the inner cap, and when a C-shaped clip that provides a vertical space which allows the outer cap to be lowered from a fixed position is removed and then the outer cap is lowered by rotating the outer cap, as like rotating in a screw-connection, to be lowered to the exposed vertical space, when the sealing membrane is lowered as the packing holder and the injection medicine bottle are lowered together with the outer cap, the injection needle punctures the sealing membrane and the injection solution is automatically mixed with the contents of the infusion container, thereby a user doesn't need to manipulate the injection needle separately when puncturing the injection needle to the injection medicine bottle, making it possible for beginners to use.

The present disclosure, wherein an injection needle is fixed at the inlet of the pouch container, an inner cap having an edge that is welded is coupled to an injection needle holder that supports the injection needle, a sealing membrane which wraps the injection needle is arranged at the inner cap so the injection needle is isolated from outside, completely blocking the infiltration of external bacteria, and a packing holder is provided on the sealing membrane to be used for sealing the injection medicine bottle with an inner packing to completely seal the surroundings of the injection medicine bottle, and before use, the C-shaped clip holds the outer cap at a predetermined height, thereby preventing the sealing membrane from being damaged by the injection needle, thereby is durable.

DETAILED DESCRIPTION OF THE INVENTION

Figure 1:
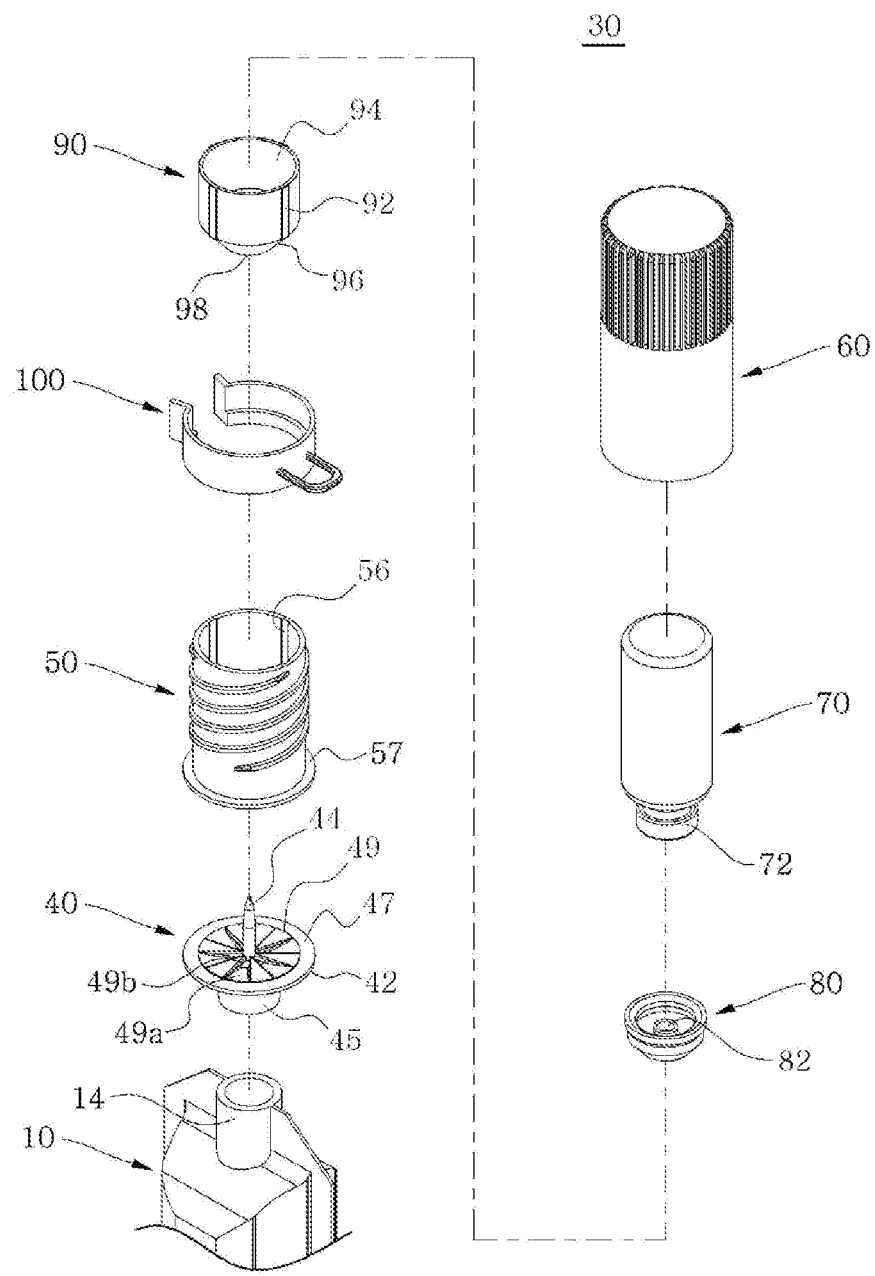
FIG. 1 is an exploded perspective view of the present disclosure.
Figure 2:
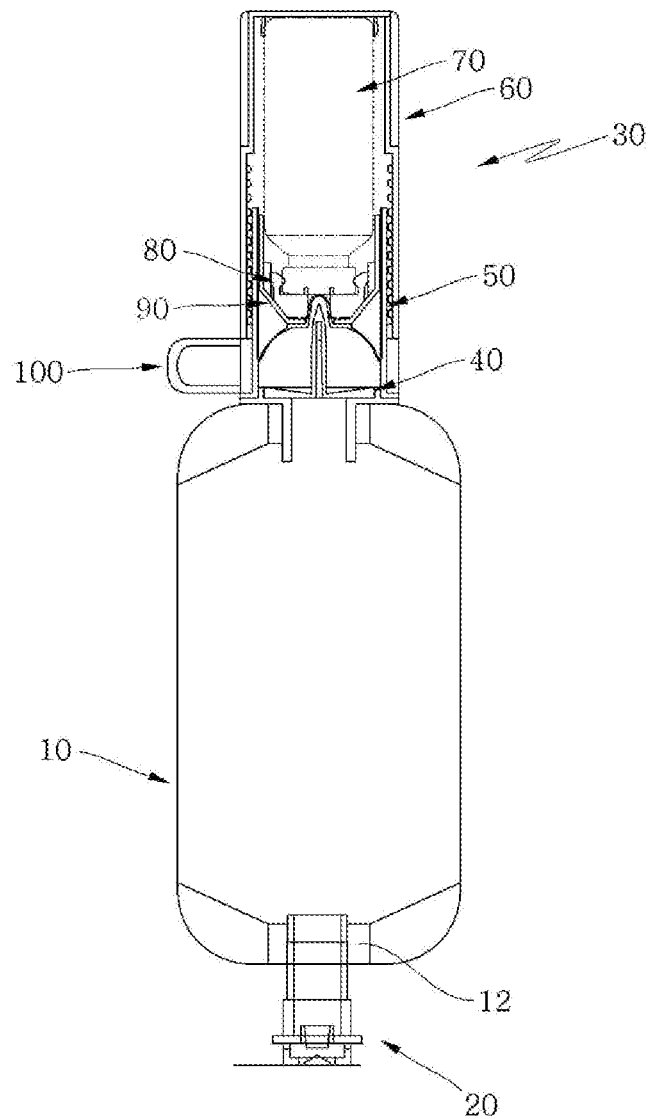
FIG. 2 is a cross-sectional view of an assembled state of the present disclosure.

Hereinafter, an embodiment of the present disclosure will be described in more detail with reference to the accompanying drawings.

According to an embodiment of the present disclosure, an infusion pouch set with a built-in injection medicine bottle having a vial function is configured to have, a discharge port 20 provided at an outlet 12 of a pouch container 10; and an injection port 30 provided at an inlet 14 of the pouch container 10; and the injection port 30 includes, an injection needle part 40 configured to have an injection needle 44 provided vertically on an upper part of an injection needle holder 42 which is welded to the inlet 14 of the pouch container 10;

an inner cap 50 having a sealing membrane 52 which is coupled to the injection needle holder 42 of the injection needle part 40, accommodates the injection needle 44 therein, and is punctured by the injection needle 44 when lowered;

an outer cap 60 which is vertically moveable along the same axis as the inner cap 50 and accommodates an injection medicine bottle 70 in an upside down state therein; and a packing holder 90 which is vertically movably coupled at an upper part of the sealing membrane 52 of the inner cap 50, and a lower part of the packing holder 90 accommodates a packing 80 which hermetically couples an inlet cover 72 with the sealing membrane 52 and has a vertical through-hole 82 at its center.

The sealing membrane 52 formed inside the inner cap 50 so as to cover the inner diameter thereof is configured to have, a protruding part 53 which is convex upward and is concave downward when the packing holder 90 is pressed, an annular plate part 54, which is provided on an upper surface of the protruding part 53 in an annular plate form, and a hemispherical protruding part 55 protrudes so as to be inserted into a vertical through-hole 82 of the packing 80 at an inner diameter part of the annular plate part 54.

The packing holder 90 is configured to have a tapered part 96 for receiving the shoulder of the injection medicine bottle 70 provided with a vertical guide 92 having a groove or protruding form perpendicularly disposed on an outer surface thereof to guide an injection to the inner cap 50 at a lower end of a tubular body part 94, which moves vertically with the inner cap 50, and a bottom plate 98 supported by the annular plate part 54 at the lower end of the tapered part 96 and has a protrusion insertion hole 97.

At an inner cap 50 portion corresponding to the vertical guide 92 having a vertical groove or protrusion form on an outer surface of the tubular body part 94 of the packing holder 90, a movement guide 56 is formed, wherein the movement guide 56 includes a protrusion form or groove formed to the vicinity of an edge of the sealing membrane 52.

The injection needle holder 42 of the injection needle part 40 is configured to have a holder tube 45 which is welded to the inlet 14 of the pouch container 10, a support plate 47 coupled to an upper end of the holder tube 45 for supporting an injection needle head part 46 having an injection needle through-hole 48 through which the injection needle tube penetrates, and a coupling dam 49 protruding at the upper part of the edge of the support plate 47 so as to be coupled with the inner cap 50.

The infusion pouch set with a built-in injection medicine bottle having a vial function according to the present disclosure may have a horizontal ring 57 for supporting a C-shaped clip 100 formed integrally with a lower end of the inner cap 50 which is fixed to the outer diameter of the coupling dam 49 and is located on the inner diameter of the outer cap 60.

The C-shaped clip 100 is configured to wrap the outer circumference of the inner cap 50 between the lower end of the outer cap 60 and the upper part of the horizontal ring 57 and to spread its opening so as to be horizontally separated when it is pulled outwardly. It is preferable that a handle ring protruding toward the opposite side of an opening portion is additionally provided at middle portion of the C-shaped clip 100 so as to be easily separated. However, another form in which a pulling function is performed by a ring, a protrusion or the like may be adopted.

The bottom surface between the coupling dam 49 and the injection needle 44 may be formed with an inclined surface 49a so as to be inclined from the coupling dam 49 downwards toward the perimeter of the injection needle 44, and at the perimeter of the inclined surface 49a and the injection needle 44, an inclined through-hole 49b may be formed.

The holder tube 45 and the injection needle holder 42 of the injection needle part 40 of the present disclosure are hermetically welded to the inlet 14 of the pouch container 10. Since the welding technique itself is a well-known technique, it is described simply as being welded.

The support plate 47 of the injection needle holder 42 and the horizontal ring 57 of the inner cap 50 of the present disclosure are also welded. Although hook-coupling or screw-coupling means can be used, it is preferable to use a welding method for the purpose of providing airtightness when medicine is used.

In the present invention, infusion solution is first filled into the pouch container 10 and then a discharge port and an injection port are formed, and the outlet 12 and inlet 14 are welded to be sealed.

In use, the C-shaped clip 100 is separated to expose the lower end of the inner cap 50 and the horizontal ring 57 by grasping the handle of the C-shaped clip 100 and pulling it toward the opposite side of the open portion. In this case, a space is generated corresponding to the height of the C-clip 100. Therefore, when the outer cap 60 is rotated in a screw rotating manner, the external screw 58 along the inner cover 50 and the internal screw of the outer cap 60 are screw-coupled, and the outer cap 60 is lowered.

Figure 3:
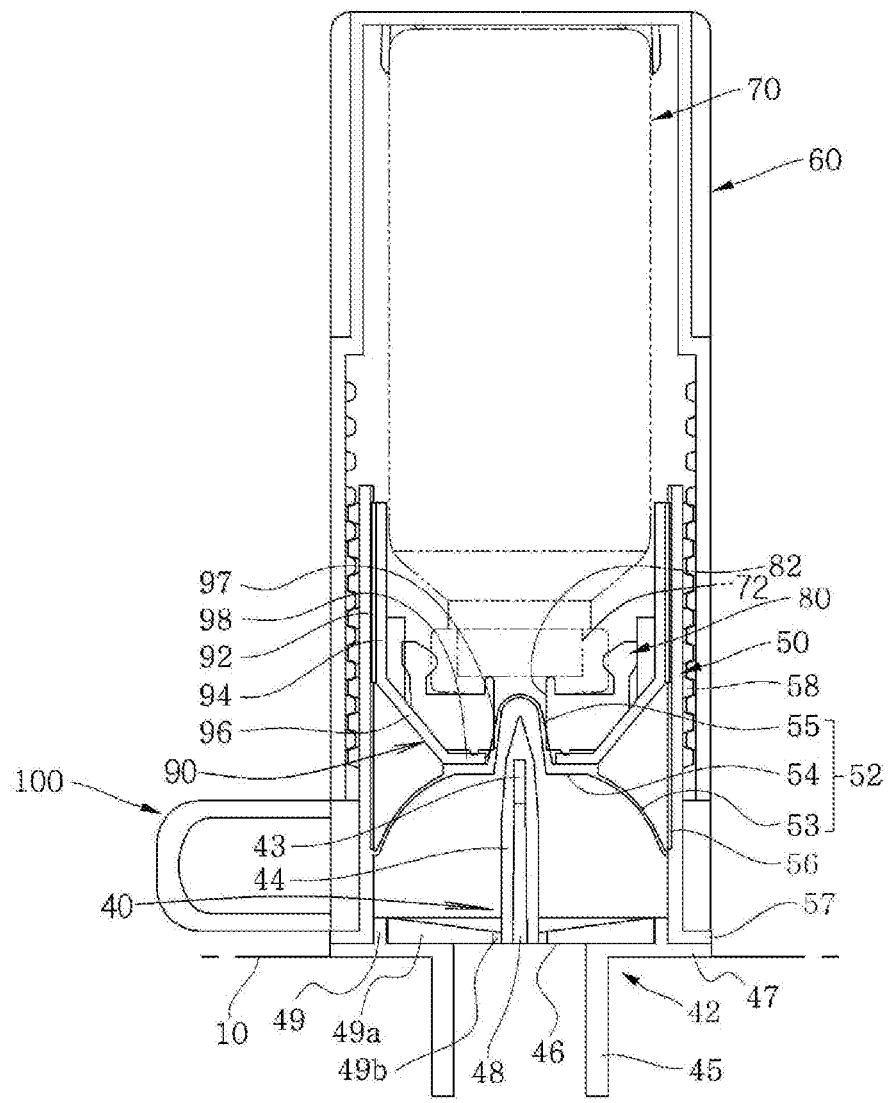
FIG. 3 is an enlarged cross-sectional view of an injection port of the present disclosure.
Figure 4:
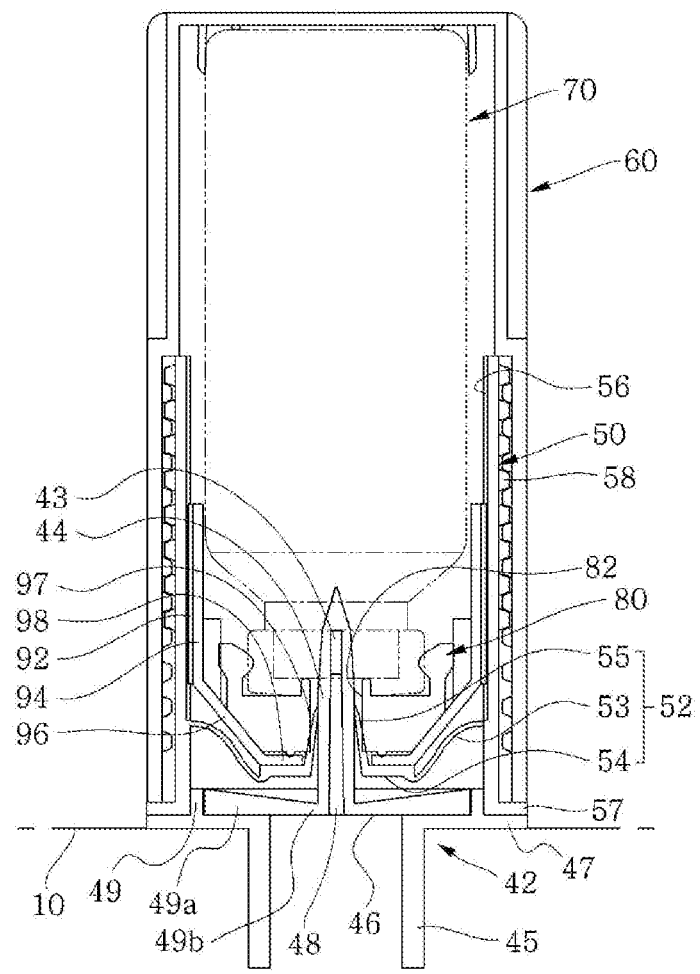
FIG. 4 is a cross-sectional view of the usage state of the present disclosure.

When the outer cap 60 is lowered, the injection medicine bottle 70 accommodated inside the outer cap 60 is lowered at the same time. The injection medicine bottle 70 and the inlet cover 72 are sealed to push the packing 80 having a vertical through-hole 82 in its center and the packing 80 tends to rotate the packing holder 90 while pushing. However, the outer surface of the packing holder 90 has a vertical guide 92 which is coupled with a movement guide 56 of the inner diameter part of the inner cap 50 in a protrusion-groove coupled manner so that the vertical guide 92 is lowered vertically. In this case, in the initial coupling with the vertical through-hole 82 and protrusion insertion hole 97 of the bottom plate 98, as shown in FIG. 3, a hemispherical protruding part 55 is inserted so as to be in a protruding state. As a result, the packing holder 90 is lowered vertically while the bottom plate 98 of the packing holder 90 pushes the annular plate part 54 downward to cause the protruding part 52 to start becoming concave. At the same time, the distal end of the injection needle 44 punctures the hemispherical protruding part 55 in a fixed state, and then the injection needle 44 punctures the inlet cap 72 of the injection medicine bottle 70 to form the state shown in FIG. 4. Thus, the medicinal solution in the injection medicine bottle is naturally supplied through the injection needle hole 43 of the injection needle 44, and is mixed with the infusion liquid via the injection needle through-hole 48.

It is a well-known technique to use other infusion needles to discharge to the body's blood vessels through the discharge port 20 of the outlet 12, and the explanation of the discharge is omitted.

In the present invention, when the infusion container cannot be erected vertically while being transported or stored, even if the infusion solution in the infusion container moves to the space between the sealing membrane 52 and the supporting plate 47 through the injection needle hole 43 of the injection needle 44, the bottom surface of the support plate 47 forms an inclined surface 49a, and the lower end of the inclined surface 49a forms an inclined through-hole 49b communicating with the inner part of the infusion container so as to return the infusion liquid to its original position inside the infusion container again without any problems in use and acts to erase the impression of the infusion liquid that seems to flow downwards.

DESCRIPTION OF SYMBOLS

10: pouch container
12: outlet
14: inlet
20: discharge port
30: injection port
40: injection needle part
42: injection needle holder
43: injection needle hole
44: injection needle
45: holder tube
46: injection needle head part
47: support plate
48: injection needle through-hole
49: coupling dam
49a: inclined surface
49b: inclined through-hole
50: inner cap
52: sealing membrane
53: protruding part 54: annular plate part
55: hemispherical protruding part
56: movement guide
57: horizontal ring
60: outer cap
70: injection medicine bottle
72: inlet cover
80: packing
82: vertical through-hole
90: packing holder
92: vertical guide
94: tubular body part
96: tapered part
97: insertion hole
98: bottom plate
100: C-shaped clip

What is claimed is:

1. An infusion pouch set with a built-in injection medicine bottle having a vial function comprising:
   a discharge port (20) provided at an outlet (12) of a pouch container (10); and
   an injection port (30) provided at an inlet (14) of the pouch container (10); wherein
   the injection port (30) comprises:
   an injection needle part (40) configured to have an injection needle (44) provided vertically on an upper part of an injection needle holder (42) wherein the injection needle part (40) is welded to the inlet (14) of the pouch container (10);
   an inner cap (50) having a sealing membrane (52) which is coupled to the injection needle holder (42) of the injection needle part (40), accommodates the injection needle (44) therein, and is punctured by the injection needle (44) when lowered;
   an outer cap (60) which is vertically moveable along the same axis as the inner cap (50) and accommodates an injection medicine bottle (70) in an upside down state therein; and
   a packing holder (90) which is vertically movably coupled at an upper part of the sealing membrane (52) of the inner cap (50), and wherein a lower part of the packing holder (90) accommodates a packing (80) which hermetically couples an inlet cover (72) of the injection medicine bottle (70) with the sealing membrane (52) and has a vertical through-hole (82) at its center.

2. The infusion pouch set of claim 1, wherein the sealing membrane (52) is formed inside the inner cap (50) so as to cover the inner diameter thereof and comprises, a protruding part (53) which is convex upward in a first state and is concave downward in a second state when the packing holder (90) is pressed,
   an annular plate part (54), which is provided on an inner side of the protruding part (53) in an annular plate form, and
   a hemispherical protruding part (55) protruded upward so as to be inserted into a vertical through-hole (82) of the packing (80) at an inner diameter part of the annular plate part (54).

3. The infusion pouch set of claim 2, wherein the packing holder (90) comprises a tapered part (96) for receiving a shoulder of the injection medicine bottle (70) and is provided with a vertical guide (92) having a groove or protruding form vertically disposed on an outer surface of a tubular body part (94) to guide an injection to the inner cap (50), and
   a bottom plate (98) supported by the annular plate part (54) at the lower end of the tapered part (96) and having a protrusion insertion hole (97).

4. The infusion pouch set of claim 3, wherein at an inner cap (50) portion corresponding to the vertical guide (92) having the vertically disposed groove or protrusion form on the outer surface of the tubular body part (94) of the packing holder (90), a movement guide (56) is formed, wherein the movement guide (56) includes a protrusion form or groove formed toward an edge of the sealing membrane (52).

5. The infusion pouch set of claim 1, wherein the injection needle holder (42) of the injection needle part (40) includes a holder tube (45) which is welded to the inlet (14) of the pouch container (10), a support plate (47) coupled to an upper end of the holder tube (45) for supporting an injection needle head part (46) having an injection needle through-hole (48) through which the injection needle tube head part penetrates, and a coupling dam (49) protruding at the upper part of the edge of the support plate (47) so as to be coupled with the inner cap (50).

6. The infusion pouch set of claim 5, wherein a horizontal ring (57) for supporting a C-shaped clip (100) is formed integrally at a lower end of the inner cap (50) which is fixed to the coupling dam (49) and is located on the inner diameter of the outer cap (60).

7. The infusion pouch set of claim 6, wherein the C-shaped clip (100) is configured to wrap the outer circumference of the inner cap (50) between the lower end of the outer cap (60) and the upper part of the horizontal ring (57) and includes a vertical opening which is configured to be widened so as to have the C-shaped clip (100) horizontally separated when it is pulled outwardly.

8. The infusion pouch set of claim 5, wherein a bottom surface between the coupling dam (49) and the injection needle (44) is formed with an inclined surface (49a) so as to be inclined from the coupling dam (49) downwards toward the perimeter of the injection needle (44), and at the perimeter of the inclined surface (49a) and the injection needle (44), an inclined through-hole (49b) is formed.

* * * * *